(12) United States Patent
Hartselle

(10) Patent No.: US 8,323,214 B2
(45) Date of Patent: Dec. 4, 2012

(54) ORAL TESTING DEVICES AND METHODS

(76) Inventor: Larry Hartselle, Huntsville, AL (US)

( * ) Notice: Subject to any disclaimer, the term of this patent is extended or adjusted under 35 U.S.C. 154(b) by 26 days.

(21) Appl. No.: 12/913,270

(22) Filed: Oct. 27, 2010

(65) Prior Publication Data

US 2012/0109009 A1    May 3, 2012

(51) Int. Cl.
*A61B 5/00* (2006.01)
(52) U.S. Cl. .................... 600/584; 600/573; 600/582
(58) Field of Classification Search .................. 600/573, 600/576, 582, 584
See application file for complete search history.

(56) References Cited

U.S. PATENT DOCUMENTS

| | | | |
|---|---|---|---|
| 6,372,516 B1* | 4/2002 | Sun | 436/518 |
| 2001/0034068 A1* | 10/2001 | Spivey et al. | 436/518 |
| 2011/0275162 A1* | 11/2011 | Xie et al. | 436/164 |

* cited by examiner

*Primary Examiner* — Brian Szmal
*Assistant Examiner* — Emily Lloyd
(74) *Attorney, Agent, or Firm* — Ann I. Dennen; Lanier Ford Shaver & Payne, P.C.

(57) ABSTRACT

An oral testing device has a housing comprising a window for visually exposing test strips within the housing and a donor sample pad coupled to a first end of the housing. In addition, the oral testing device has a mirror hingedly coupled to a second end of the housing positioned for viewing the test strips when the donor sample pad is inserted within a donor's mouth.

20 Claims, 5 Drawing Sheets

ORAL TESTING DEVICES AND METHODS

BACKGROUND

There are a variety of tests that are used to test whether a donor has partaken in any number of drugs. There are urine tests in which a donor deposits his/her urine into a cup, and test strips are submerged in the urine. The test strips have drug indication lines that appear or do not appear based on the presence or absence of drugs in the urine.

In addition, saliva tests exist in which a donor inserts a testing device in his/her mouth. The saliva is then tested, via the testing device, to determine whether the donor has partaken in any number of drugs.

The saliva testing devices are often difficult to use. In this regard, it is often difficult to get enough saliva on the test strips to ensure an accurate test. Further, it is often difficult to know when an adequate amount of saliva has been collected to run the test because the saliva must be transferred to the test to determine if an adequate amount of saliva has been collected to run the tests, and because the test strips are not visible to the donor when the saliva is being collected.

DESCRIPTION OF DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the figures.

DESCRIPTION

The present disclosure relates to oral testing devices. In particular, an exemplary oral testing device in accordance with an embodiment of the present disclosure comprises a housing having a first end that is coupled to a donor sample pad for insertion into a donor's mouth. On a top side of the housing is a window that exposes at least one test strip enclosed within the housing.

In operation, as the donor's saliva saturates the donor sample pad, the saliva is absorbed by the test strips. As saliva is absorbed by the strips, the strips change colors, e.g., pink. If no drug is detected, a line will appear for each drug that is tested. If a drug(s) is detected, a line will not appear for the drug(s) that is being tested. There are also control lines at an end of the strips that appear to indicate that the test ran properly. A mirror is hingedly coupled to a second end of the housing. As the donor's saliva is absorbed by the test strips, the donor can view in the mirror when enough saliva has been absorbed to change the color of the test strips indicating that enough saliva has been absorbed to run the test properly.

Figure 1:
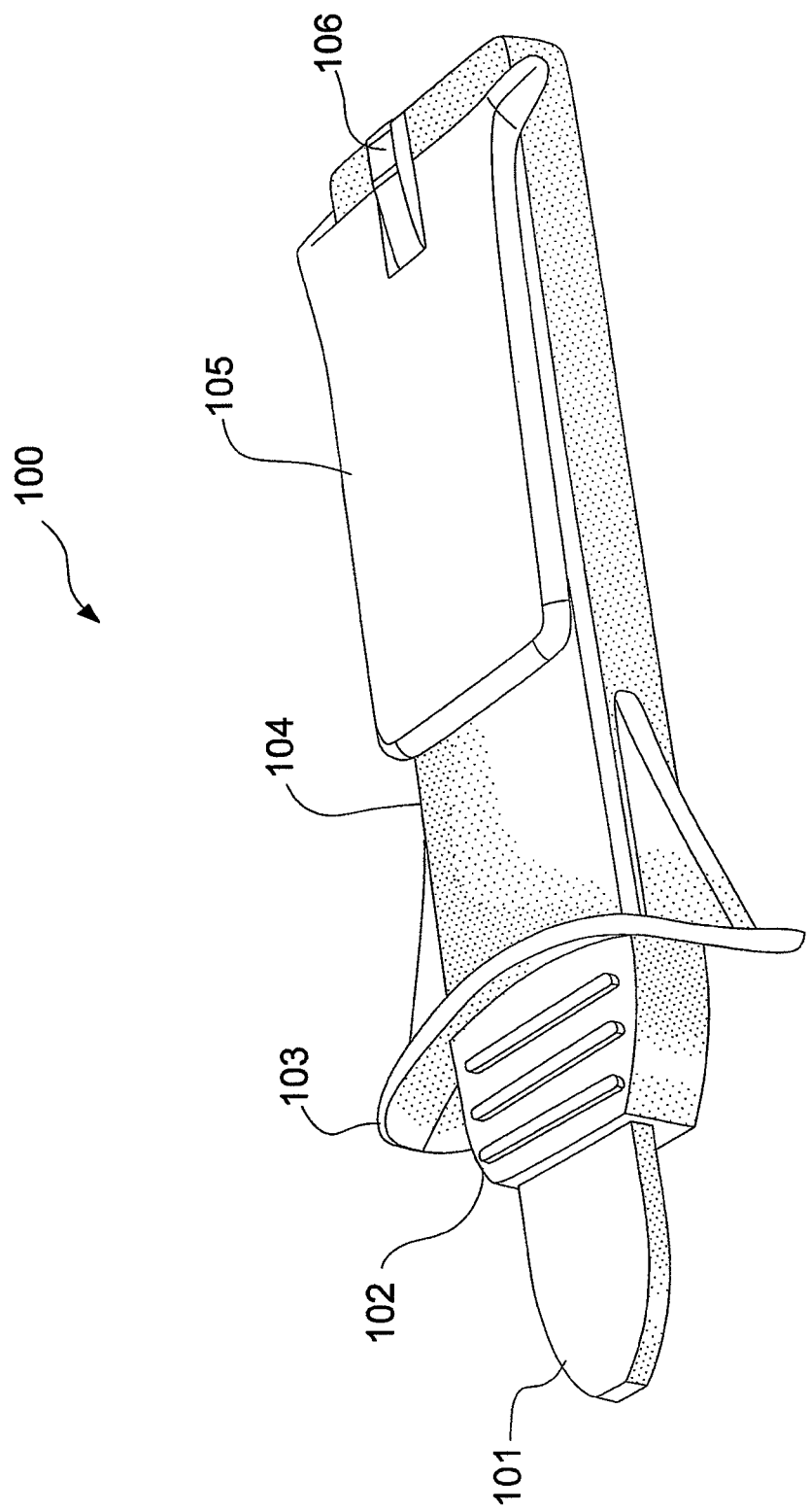
FIG. 1 is a perspective view of an exemplary oral testing device with an attached mirror in a closed position in accordance with an embodiment of the present disclosure.

FIG. 1 depicts an exemplary oral testing device 100 in accordance with an embodiment of the present disclosure. The oral testing device 100 comprises a housing 104.

In one embodiment, the housing 104 is composed of a plastic-type material. For example, the housing 104 may be made out of molded plastic. The housing 104 may be made out of other types of materials known in the art or future-developed in other embodiments of the oral testing device 100.

A donor sample pad 101 is coupled to an end of the housing. The donor sample pad 101 is inserted through a mouthpiece 102. The mouthpiece 102 terminates at a lip stop 103.

In one embodiment, the donor sample pad 101 is made out of an absorbent material, such as, for example, a cotton-based material. The material absorbs saliva of a donor when the donor sample pad 101 is held within the donor's mouth for a period of time. The donor sample pad 101 may be made out of other types of absorbent materials known in the art or future-developed in other embodiments of the oral testing device 100.

The oral testing device 100 further comprises a mirror 105. The mirror 105 is hingedly coupled, via a hinge 106, to the housing 104. Notably, FIG. 1 shows the mirror 105 in a closed position.

Figure 2:
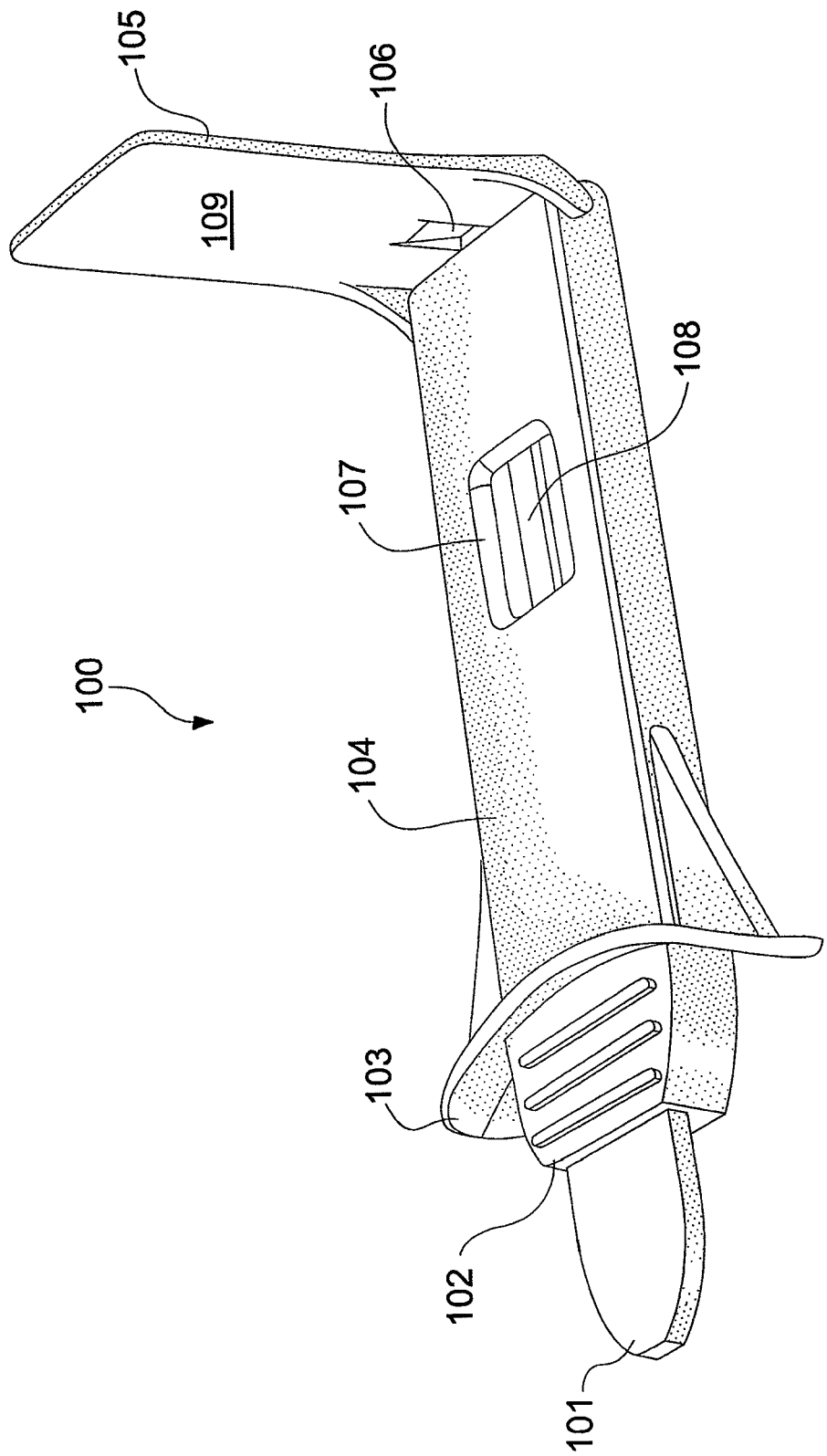
FIG. 2 is a perspective view of the oral testing device, such as is depicted in FIG. 1, with the attached mirror in an open position.

FIG. 2 depicts another perspective view of the oral testing device 100. FIG. 2 depicts the donor sample pad 101 inserted through the mouthpiece 102 that terminates with the lip stop 103. Further, FIG. 2 depicts the mirror 105 coupled via the hinge 106 to the housing 104.

FIG. 2 further depicts a window 107 within the housing 104. The window 107 is transparent so that a plurality of test strips 108 can be viewed through the window 107. In one embodiment, the window 107 comprises a plastic transparent cover that protects the test strips 108 from moisture and impurities.

In one embodiment, the test strips 108 comprise a plurality of drug indicators. For example, the test strips 108 may have a drug indication line and corresponding text for cocaine (COC), Tetrahydrocannabinol (THC), methamphetamine (MET), opiates (OPI), or amphetamine (AMP). Thus, as saliva is absorbed by the test strips 108, the test strips 108 change color, e.g., white to pink, and drug indication lines for each drug appear to indicate that such corresponding drug is not present in the saliva. Notably, if one of the drugs is present in the saliva, a line will not appear. Note that the drugs listed are for exemplary purposes, and the saliva may be tested for other drugs known in the art.

When the mirror 105 is in an open position, as shown in FIG. 2, a reflective side 109 of the mirror 105 is positioned such that light from the test strips 108 is reflected by the reflective side 109 of the mirror 105. Thus, when the donor sample pad 101 is inserted in the donor's mouth, as shown herein with reference to FIG. 4, the donor can see the test strips 108 in the mirror 105. By viewing the test strips 108 as they change color in response to saliva, the donor knows when enough saliva has been absorbed to run the test properly.

Figure 3:
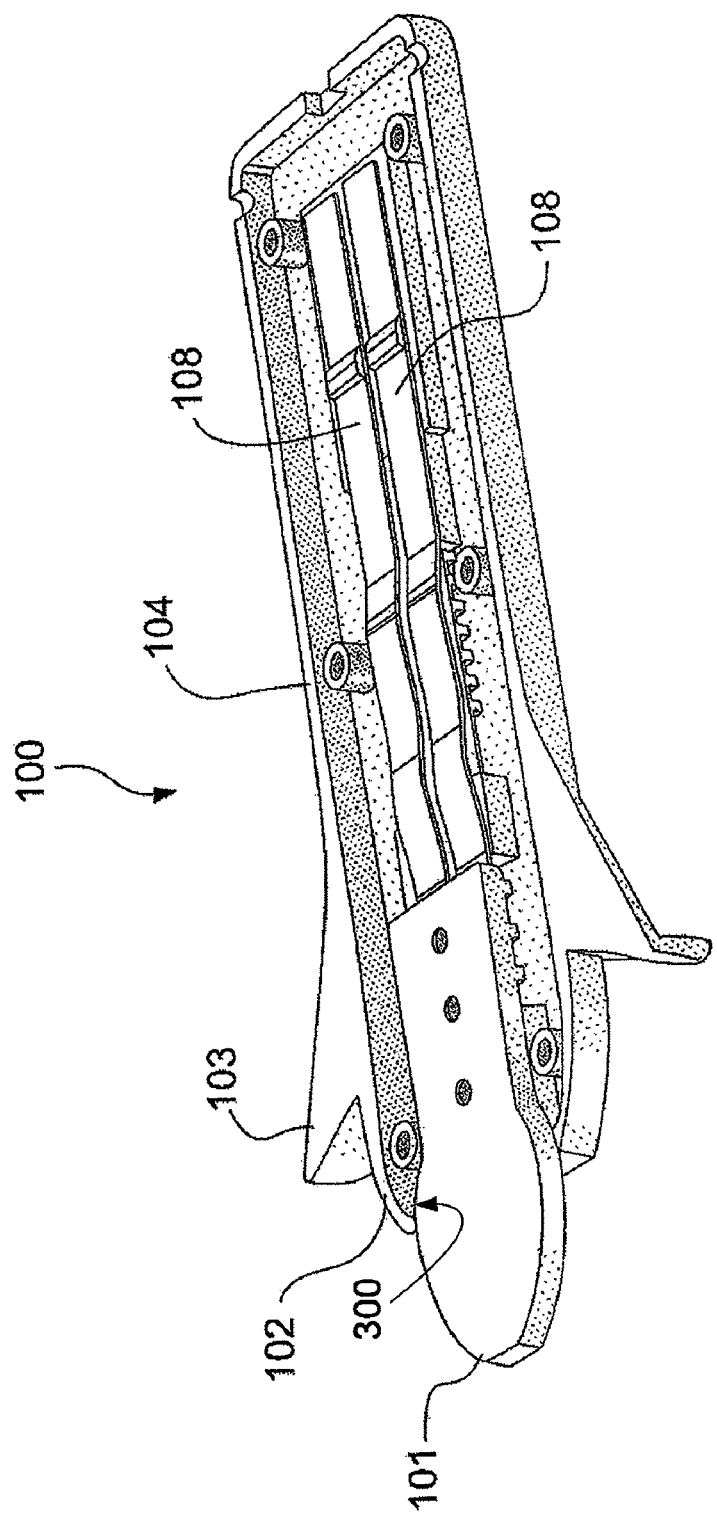
FIG. 3 is a perspective view of the oral testing device, such as is depicted in FIG. 1, showing the housing of the oral testing device removed from a plurality of testing strips.

FIG. 3 depicts a perspective view of the oral testing device 100 with a top portion of the housing 104 removed for illustrative purposes. The donor sample pad 101 is inserted through an opening 300 in the mouthpiece 102 and extends pass the lip stop 103 to the test strips 108.

The donor sample pad 101 contacts the test strips 108. Thus, there is fluid communication between the donor sample pad 101 and the test strips 108. Hence, when a donor places the donor sample pad 101 in his/her mouth, the donor's saliva is absorbed by the donor sample pad 101. As saliva is absorbed by the donor sample pad 101, saliva transfers from the donor sample pad 101 to the test strips 108.

The saliva is absorbed by the test strips 108 and moves from the donor sample pad 101 through reagent pads on the test strips 108 toward the mirror hinge 106 (FIG. 2). As the saliva moves through the test strips 108, the test strips 108 change colors, e.g., white to pink, as described hereinabove. Once the color changes, enough saliva has been absorbed to run the test properly. The test strips 108 may also change to another color, such as blue, if other technology besides colloidal gold antibodies is utilized.

When the donor sample pad 101 is in the donor's mouth, the donor can view changes in the window 107 (FIG. 2) via the mirror 105 (FIG. 2). Thus, the donor knows when saliva has been absorbed enough to perform the drug test on the saliva by the changing of the color of the test strips 108, e.g., white to pink. Once the donor views that saliva has been absorbed so that the tests are being performed on the saliva, the donor can remove the oral testing device 100 from the donor's mouth.

Figure 4:
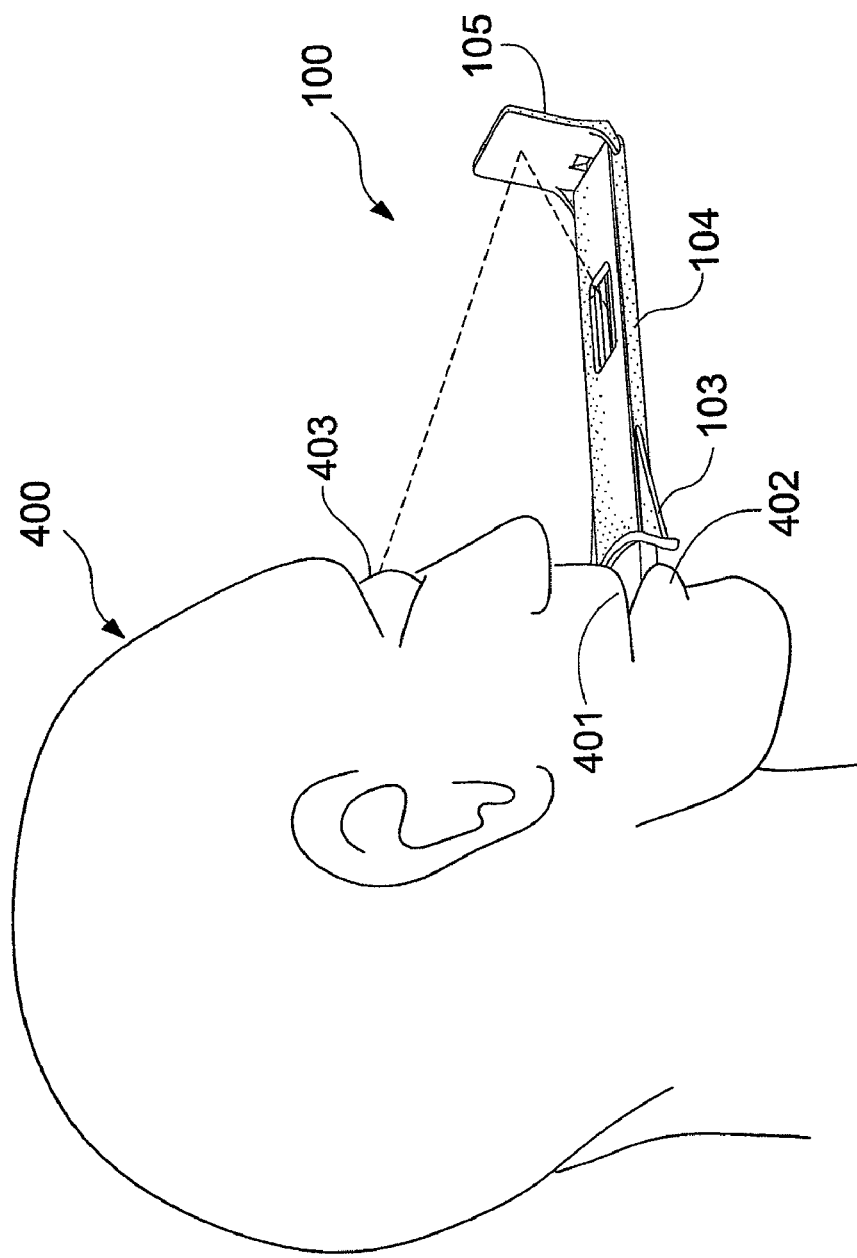
FIG. 4 is a side view of a user using the oral testing device, such as is depicted in FIG. 1.

FIG. 4 depicts a donor 400 that is using the oral testing device 100. As shown, the donor 400 inserts the donor sample pad 101 into his/her mouth 401. In this regard, the donor's mouth 401 fits around the mouthpiece 102, and the oral testing device 100 is inserted into the donor's mouth 401 until the donor's lips 402 reach the lip stop 103.

In the housing 104 is the window 107, which shows the test strips 108 (FIG. 2). In use, the mirror 105 is placed in an open position.

As saliva is absorbed by the test strips 108, the test strips 108 change color, e.g., white to pink. Light from the window 107 having the test strips 108 is reflected from the mirror 105. Such reflection can be viewed by the donor's eyes 403. Thus, when the donor 400 sees the test strips 108 change colors, the donor 400 can remove the oral testing device from the donor's mouth 401.

Figure 5:
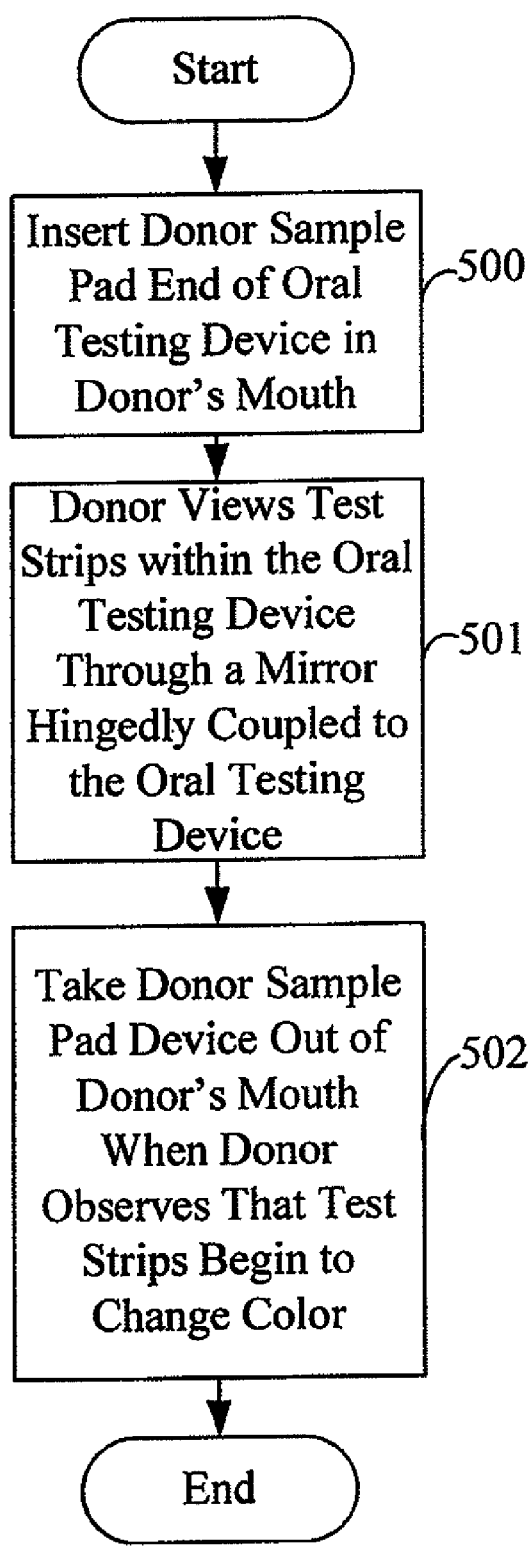
FIG. 5 is a flowchart for an exemplary method in accordance with an embodiment of the present disclosure.

FIG. 5 depicts a flowchart for an exemplary method in accordance with an embodiment of the present disclosure. In step 500, the donor inserts by hand or otherwise the donor sample pad 101 (FIG. 1) of the oral testing device 100 (FIG. 1) in the donor's mouth 401 (FIG. 4).

In step 501, the donor views the test strips 108 (FIG. 2) within the oral testing device 100 through a mirror 105 hingedly coupled to the oral testing device housing 104 (FIG. 2). The donor views the test strips 108 through the window 107 (FIG. 2) that is within the housing 104.

In step 502, the donor removes the donor sample pad 101 from the donor's mouth 401 when the test strips 108 change color indicating that enough saliva has been absorbed to run the test properly.

The invention claimed is:

1. An oral testing device, comprising:
   a housing comprising a window for visually exposing a saliva test strip within the housing;
   a donor sample pad coupled to a first end of the housing, wherein the donor sample pad is in fluid communication with the saliva test strip, and the donor sample pad is configured to transfer saliva to the saliva test strip; and
   a mirror directly attached to a second end of the housing, wherein the mirror is configured to be positioned such that a reflection of the saliva test strip via the window is reflected by the mirror such that the reflection is in the field of view of the donor.

2. The oral testing device of claim 1, wherein the housing comprises a mouthpiece.

3. The oral testing device of claim 2, wherein the housing further comprises a lip stop.

4. The oral testing device of claim 3, wherein the lip stop is positioned contiguous with the sample pad and the sample pad extends outwardly from the lip stop.

5. The oral testing device of claim 1, wherein the donor sample pad extends through an opening in a mouthpiece.

6. The oral testing device of claim 5, wherein the donor sample pad contacts the saliva test strip.

7. The oral testing device of claim 6, wherein the donor sample pad is positioned contiguous relative to the saliva test strip.

8. The oral testing device of claim 1, wherein the mirror is directly attached to the second end of the housing via a hinge.

9. The oral testing device of claim 8, wherein the hinge is configured to place the mirror in an open position where the mirror is configured to reflect the saliva test strip via the window such that the reflection is in the field of view of the donor, and the hinge is further configured to place the mirror in a closed position, where the mirror covers the window.

10. The oral testing device of claim 1, wherein the saliva test strip is a plurality of saliva test strips.

11. The oral testing device of claim 1, wherein the housing is composed of a plastic material.

12. The oral testing device of claim 11, wherein the housing is made of molded plastic.

13. The oral testing device of claim 1, wherein the donor sample pad is made out of a cotton-based material.

14. The oral testing device of claim 1, wherein the window comprises a plastic transparent cover.

15. The oral testing device of claim 1, wherein the saliva test strip is configured to test for one or more of cocaine, tetrahydrocannabinol (THC), methamphetamine, opiates, and amphetamine.

16. A method for ensuring a proper saliva sample size, the method comprising:
   providing an oral testing device comprising:
      a housing comprising a window for visually exposing a saliva test strip within the housing, wherein the saliva test strip is configured to provide a visual indication when a proper saliva sample size is collected;
      a donor sample pad coupled to a first end of the housing, wherein the donor sample pad is in fluid communication with the saliva test strip, and the donor sample pad is configured to transfer saliva to the saliva test strip; and
      a mirror directly attached to a second end of the housing, wherein the mirror is configured to be positioned such that a reflection of the saliva test strip via the window is reflected by the mirror such that the reflection is in the field of view of the donor;
   inserting the donor sample pad of the oral testing device into the mouth of the donor; and
   removing the donor sample pad from the donor's mouth when the saliva test strip indicates the presence of a proper saliva sample size as viewed by the reflection of the test strip via the mirror to the field of vision of the donor.

17. The method of claim 16, wherein the visual indication of a proper saliva sample size is a change in color.

18. A method for testing a donor for drug use, the method comprising:
   providing an oral testing device comprising:
      a housing comprising a window for visually exposing a saliva test strip within the housing, wherein the saliva test strip is configured to indicate the presence of a drug in the user's saliva;
      a donor sample pad coupled to a first end of the housing, wherein the donor sample pad is in fluid communication with the saliva test strip, and the donor sample pad is configured to transfer saliva to the saliva test strip; and a mirror directly attached to a second end of the housing, wherein the mirror is configured to be positioned such that a reflection of the saliva test strip via the window is reflected by the mirror such that the reflection is in the field of view of the donor;

inserting the donor sample pad of the oral testing device into the mouth of the donor; and removing the donor sample pad from the donor's mouth when the saliva test strip indicates the presence of a proper saliva sample size as viewed by the reflection of the test strip via the mirror to the field of vision of the donor, wherein upon absorption of a proper saliva sample size, the test strip also provides a visual indication of whether or not the drug is present in the saliva.

19. The method of claim 18, wherein the visual indication of a proper saliva sample size is a change in color.

20. The method of claim 18, wherein the saliva test strip is configured to test for one or more of cocaine, tetrahydrocannabinol (THC), methamphetamine, opiates, and amphetamine.

* * * * *